US00PP29120P2

(12) United States Plant Patent
Olesen

(10) Patent No.: US PP29,120 P2
(45) Date of Patent: Mar. 20, 2018

(54) MINIATURE ROSE PLANT NAMED 'POULPAR097'

(50) Latin Name: ***Rosa* hybrid**
Varietal Denomination: Poulpar097

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/330,296

(22) Filed: Sep. 6, 2016

(51) Int. Cl.
*A01H 5/02* (2006.01)

(52) U.S. Cl.
USPC ..... Plt./121

(58) Field of Classification Search
USPC ..... Plt./121
CPC ..... A01H 5/0222
See application file for complete search history.

(56) References Cited

PUBLICATIONS http://www.poulsenroser.com/assortment/rose-collections/parade/tena.aspx; No date; 1 page.*

* cited by examiner

*Primary Examiner* — Kent L Bell

(57) ABSTRACT

A new garden rose plant of the miniature class which has abundant, pink blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar097'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpar097', originated as a single seedling from the stated cross.

The new variety may be distinguished from its male pollen parent and female seed parent primarily by the following characteristics. The male pollen parent plant near white flowers, while the new variety has pink blend flowers. The female seed parent plant has medium red flowers, while the new variety has pink blend flowers.

The objective of the hybridization of this rose variety was to create a new and distinct variety for garden use with unique qualities, such as:

1. Uniform and abundant pink blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar097' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpar097' was selected in the spring of 2011 by the inventor as a single plant from the progeny of the aforementioned hybridization.

Asexual reproduction of 'Poulpar097' by traditional budding and rooted cuttings was first done by Mogens N. Olesen in the nursery in Fredensborg, Denmark in July, 2011. This initial and other subsequent asexual propagations conducted in controlled environments have demonstrated that the characteristics of 'Poulpar097' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar097'.

Specifically illustrated in FIG. 1 of the drawing are open flowers, viewed from above and the side, flower petals detached, sepals detached showing receptacle and reproductive flower parts.

DETAILED DESCRIPTION OF THE VARIETY

Figure 1:
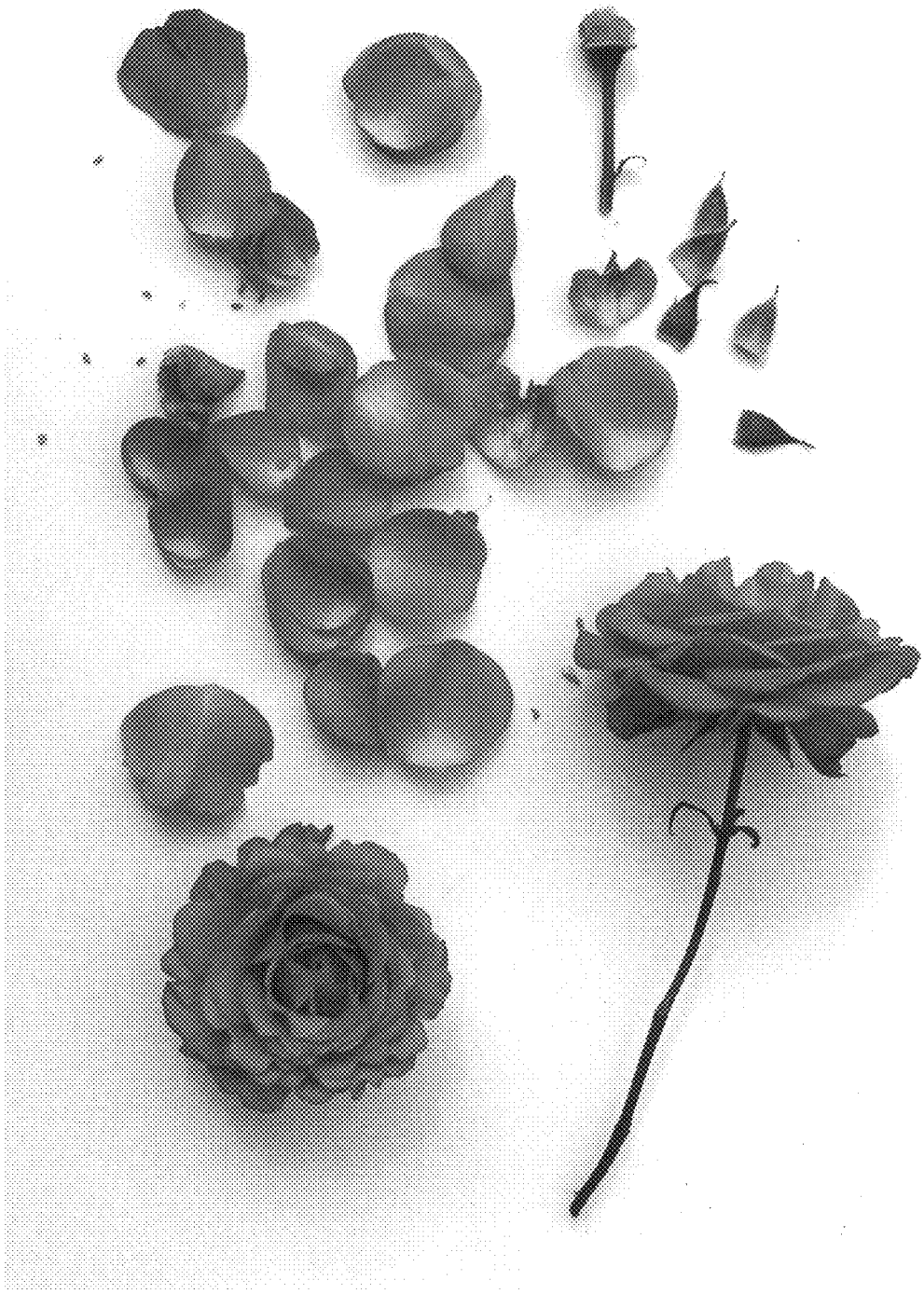
Figure 2:
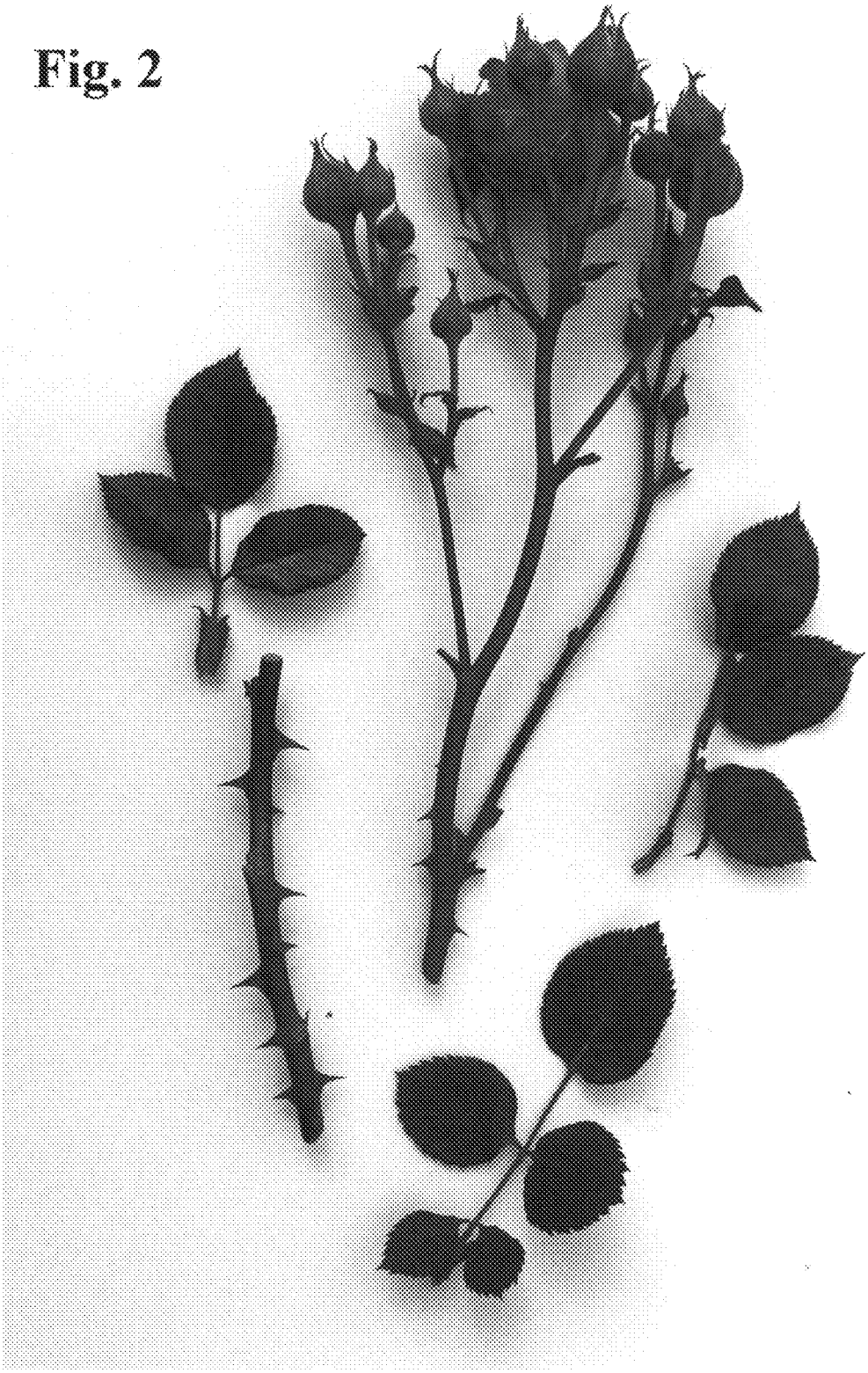
FIG. 2. shows a flowering branch with many flower buds, bare stem, and leaves. Plants shown are 2 years of age.

The following is a description of 'Poulpar097', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poultin', U.S. Plant Pat. No. 10,164 are compared to 'Poulpar097' in Chart 1.

CHART 1

| | 'Poulpar097' | 'Poultin' |
|---|---|---|
| Petal Count | 45 | 20-25 |
| Flower Diameter | 65 mm | 44 to 50 |
| Petal upper surface | Red-Purple Group N57C splashed with Red-Purple Group 63C. | Red-Purple Group 58B |

FLOWER AND FLOWER BUD

Blooming habit: Continuous.

Flower bud:

*Size.*—Upon opening, 20 mm in length from base of receptacle to end of bud. Bud diameter is 16 mm.

*Bud form.*—Globose.

*Bud color.*—As sepals divide petals are Red Group 53C.

*Sepal inner surface.*—Color: Yellow-Green Group 147C. Surface: Lightly pubescent.

*Sepal outer surface.*—Color: Yellow-Green Group 144A with Greyed-Orange Group 166A and Greyed-Purple Group 185A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—15 mm long, 8 mm wide.

*Receptacle.*—Texture: Smooth. Size: 12 mm in height, 8 mm wide. Color: Yellow-Green Group 144A. Shape: Funnel.

*Pedicel.*—Surface: Smooth. Length: 25 to 30 mm. Diameter: 3 mm on average. Color: Yellow-Green Group 144C with intonations of Greyed-Red Group 180B. Strength: Average.

*Peduncle.*—Length: 3 to 10 cm. Diameter: About 3 to 4 mm. Color: Greyed-Purple Group 183A. Texture: Smooth.

Flower bud development: Flower buds are borne in clusters of 3 to 5 flower buds per stem.

Flower bloom:

*Fragrance.*—None.

*Duration.*—The blooms have a duration on the plant of approximately 7 to 10 days. Petals fall cleanly away from plant after flowers have fully matured.

*Size.*—Flower diameter is 65 mm when open. Flower depth is 30 mm.

*Flower shape.*—Rosette, double flower with many slightly overlapping petals of different sizes.

*Shape of flower, side view.*—The upper portion is convex. The lower portion is somewhat concave.

Petalage: Under normal conditions, flowers have 45 petals.

General tonality of flower: Open flowers are Red-Purple Group N57C.

Petal color:

*Upon opening and after opening, all petals.*—Upper surface: Red-Purple Group N57C splashed with Red-Purple Group 63C. Lower surface: Red-Purple Group N57C splashed with Red-Purple Group 63C. Some petals have streaks of Green-White Group 157A.

*Petal spot.*—Upper surface: Yellow Group 11C. Lower surface: Yellow-White Group 158D.

Petals:

*Petal reflex.*—Flat.

*Margin.*—Entire and uniform, occasional cleft. No undulations.

*Shape.*—Generally rounded. Apex shape: Rounded. Base shape: Acute to rounded.

*Size.*—32 mm (l)×35 mm (w).

*Texture.*—Smooth.

*Thickness.*—Average.

Petaloids:

*Size.*—15 mm (l) by 9 mm (w).

*Quantity.*—About 8.

*Shape.*—Acute base and round apex.

*Color.*—Red-Purple Group 63C on the upper surface, and Red-Purple Group N57C splashed with Red-Purple Group 63C on the lower surface.

Reproductive flower parts:

*Pollen.*—None observed.

*Anthers.*—Size: 2 mm in length. Color: Yellow-Orange Group 23A. Quantity: 30 on average.

*Filaments.*—Color: Yellow-Orange Group 22C. Length: 4 mm.

*Pistils.*—Length: 7 mm. Quantity: 25 on average.

*Stigmas.*—Color: Yellow-Green Group 154D.

*Styles.*—Color: White Group 155A.

*Location of stigmas.*—Superior in location relative to the length of the filaments and the height of the anthers.

*Hips.*—None Observed.

PLANT

Plant growth: Upright, bushy. Plants are 30 cm in height, and 30 cm wide.

Stems:

*Color.*—Juvenile growth: Greyed-Purple Group 183B. Mature growth: Greyed-Purple Group 183B.

*Length.*—On average, canes are 15 cm from the base of the plant to the flowering portion.

*Diameter.*—6 mm.

*Internodes.*—On mature canes about 33 mm between nodes.

*Surface texture.*—Young wood: Smooth. Older wood: Smooth.

Long prickles:

*Incidence.*—About 9 prickles per 10 cm of stem.

*Size.*—Average length of prickles on mature stems is 7 mm.

*Shape.*—Upper portion is linear. Lower portion is concave.

*Color.*—Juvenile prickles: Greyed-Purple Group 183A. Mature prickles: Greyed-Purple Group 183A.

Plant foliage:

*Compound leaf.*—100 mm (l)×57 mm (w).

*Quantity.*—3 leaves per 10 cm of stem on average.

*Leaf bearing angle to the stem.*—45 degrees.

*Color of juvenile foliage.*—Upper side: Yellow-Green Group 148A. Lower side: Yellow-Green Group 144B.

*Color of mature foliage.*—Upper side: Yellow-Green Group 147A. Lower side: Yellow-Green Group 146B.

Plant leaves and leaflets:

*Stipules*.—Size: 20 mm long, 4 mm wide. Quantity: 2 per compound leaf. Shape: Linear, slightly broad based with outward extending apices. Margins: Finely serrated. Color: Yellow-Green Group 144A with intonations of Greyed-Purple Group 184A.

*Petiole*.—Length: About 16 mm. Diameter: 2 mm.

*Upper surface*.—Color: Greyed-Purple Group 184A.

*Lower surface*.—Color: Yellow-Green Group 144A.

*Rachis*.—Length: About 38 mm. Diameter: About 1.5 mm. Upper surface: Color: Greyed-Purple Group 184A.

*Lower surface*.—Color: Yellow-Green Group 144A.

*Leaflet*.—Quantity: Normally 5 leaflets. Margins: Serrated. Size: On average terminal leaflets are 40 mm long, 30 mm wide. Shape: Generally round. Base: Rounded. Apex: Slightly cuspidate and rounded. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpar097', substantially as illustrated and described herein, due to its abundant pink blend flowers, disease resistance, and extended period of bloom.

* * * * *